(12) United States Patent
Thompson, Jr. et al.

(10) Patent No.: US 10,357,588 B2
(45) Date of Patent: Jul. 23, 2019

(54) ABSORBENT ARTICLE COMPRISING POLYMERIC FOAM AND INTERMEDIATES

(71) Applicant: 3M INNOVATIVE PROPERTIES COMPANY, St. Paul, MN (US)

(72) Inventors: Delton R. Thompson, Jr., Lake Elmo, MN (US); Robert L. Rowan, Lincoln University, PA (US)

(73) Assignee: 3M Innovative Properties Company, St. Paul, MN (US)

( * ) Notice: Subject to any disclaimer, the term of this patent is extended or adjusted under 35 U.S.C. 154(b) by 983 days.

(21) Appl. No.: 14/394,109

(22) PCT Filed: Apr. 5, 2013

(86) PCT No.: PCT/US2013/035390
§ 371 (c)(1),
(2) Date: Oct. 13, 2014

(87) PCT Pub. No.: WO2013/180832
PCT Pub. Date: Dec. 5, 2013

(65) Prior Publication Data
US 2015/0080823 A1    Mar. 19, 2015

Related U.S. Application Data

(60) Provisional application No. 61/787,888, filed on Mar. 15, 2013, provisional application No. 61/652,388, filed on May 29, 2012.

(51) Int. Cl.
*A61F 13/15* (2006.01)
*A61L 15/24* (2006.01)
(Continued)

(52) U.S. Cl.
CPC .............. *A61L 15/24* (2013.01); *A61L 15/26* (2013.01); *A61L 15/28* (2013.01); *A61L 15/425* (2013.01)

(58) Field of Classification Search
CPC ............ A61F 13/53; A61F 2013/53082; A61F 2013/53081; A61F 2013/530839;
(Continued)

(56) References Cited

U.S. PATENT DOCUMENTS 2,957,207 A    10/1960    Roop
RE24,906 E    12/1960    Ulrich
(Continued)

FOREIGN PATENT DOCUMENTS

EP        0453286        10/1991
EP        1078616        2/2001
(Continued)

OTHER PUBLICATIONS

3M™ Tegaderm™ High Performance Foam Adhesive Dressing, Brochure, 2010, 8 pages.
(Continued)

*Primary Examiner* — Jacqueline F Stephens
(74) *Attorney, Agent, or Firm* — Carolyn A. Fischer (57) ABSTRACT

Absorbent articles are described comprising an absorbent composite. The absorbent composite comprises a first absorbent layer comprising a polymeric foam having an average cell size of at least 100 microns. The polymeric foam has at least one property selected from a) an indentation force deflection of less than 75 N at 50%; or b) a constant deflection compression set of less than 25% for a deflection of 50%; or a combination of a) and b); and a second absorbent layer in fluid communication with the fluid transport layer. In another embodiment, the a second absorbent layer has an average absorption capacity of at least 20 g/g. In another embodiment, a polyurethane foam is described having an average cell size of at least 100 microns. The polyurethane foam comprises the reaction product of at least one polyol component having polyethylene oxide units and
(Continued)

a polyisocyanate component that comprises at least 75 wt-% of at least one polymeric polyisocyanate that lacks urethane linkages. In some embodiments, the polyurethane foam is free of superabsorbent polymer. In some embodiments, the polyurethane foam has an average cell size up to 500 microns. In some embodiments, the polyurethane foam comprises at least 12 wt-% ethylene oxide units. Also described are various composites comprising the polyurethane foam described herein in combination with another substrate such as a second absorbent layer, a fluid impervious backsheet, and/or a fluid pervious topsheet.

19 Claims, 1 Drawing Sheet (51) Int. Cl.
*A61L 15/26* (2006.01)
*A61L 15/42* (2006.01)
*A61L 15/28* (2006.01)

(58) Field of Classification Search
CPC .......... A61L 15/24; A61L 15/26; A61L 15/28; A61L 15/425
USPC ................................ 604/369, 370, 374, 367
See application file for complete search history.

(56) References Cited

U.S. PATENT DOCUMENTS

| | | | |
|---|---|---|---|
| 3,900,030 A | 8/1975 | Bashan | |
| 4,239,043 A | 12/1980 | Gellert | |
| 4,394,930 A | 7/1983 | Korpman | |
| 4,410,571 A | 10/1983 | Korpman | |
| 4,610,678 A | 9/1986 | Weisman | |
| 4,673,402 A | 6/1987 | Weisman | |
| 4,985,467 A | 1/1991 | Kelly | |
| 5,147,345 A * | 9/1992 | Young | A61F 5/4401 428/315.9 |
| 5,201,727 A | 4/1993 | Nakanishi | |
| 5,229,427 A | 7/1993 | Madaj | |
| 5,250,581 A | 10/1993 | Gastinger | |
| 5,260,345 A * | 11/1993 | DesMarais | A61F 13/15203 428/316.6 |
| 5,387,207 A | 2/1995 | Dyer | |
| 5,472,437 A | 12/1995 | Akiyama | |
| 5,489,620 A | 2/1996 | Bleys | |
| 5,601,542 A | 2/1997 | Melius | |
| 5,719,201 A | 2/1998 | Wilson | |
| 5,730,739 A | 3/1998 | Lavash | |
| 5,763,335 A | 6/1998 | Hermann | |
| 5,853,402 A | 12/1998 | Faulks | |
| 5,948,829 A | 9/1999 | Wallajapet | |
| 6,033,769 A | 3/2000 | Brueggemann | |
| 6,034,149 A | 3/2000 | Bleys | |
| 6,107,538 A | 8/2000 | Young | |
| 6,121,509 A * | 9/2000 | Ashraf | A61L 15/60 442/301 |
| 6,156,951 A | 12/2000 | Gustafsson | |
| 6,174,929 B1 | 1/2001 | Hahnle | |
| 6,271,277 B1 | 8/2001 | Bleys | |
| 6,406,648 B1 | 6/2002 | Noel | |
| 6,417,241 B1 | 7/2002 | Huygens | |
| 6,486,378 B1 | 11/2002 | Areskoug | |
| 6,506,959 B2 | 1/2003 | Hamajima | |
| 6,515,195 B1 | 2/2003 | Lariviere | |
| 6,551,295 B1 | 4/2003 | Schmidt | |
| 6,570,057 B1 | 5/2003 | Schmidt | |
| 6,586,502 B2 | 7/2003 | Wallace | |
| 6,620,493 B2 | 9/2003 | Hasegawa | |
| 6,685,682 B1 | 2/2004 | Heinecke | |
| 6,689,934 B2 | 2/2004 | Dodge, II | |
| 6,723,892 B1 | 4/2004 | Daley | |
| 6,852,905 B2 | 2/2005 | Baker | |
| 6,855,739 B2 | 2/2005 | Becker | |
| 6,881,875 B2 | 4/2005 | Swenson | |
| 6,896,669 B2 | 5/2005 | Krautkramer | |
| 6,977,323 B1 | 12/2005 | Swenson | |
| 6,989,005 B1 * | 1/2006 | LaVon | A61F 13/505 604/368 |
| 7,189,768 B2 | 3/2007 | Baran, Jr. | |
| 7,329,715 B2 | 2/2008 | Wang | |
| 7,781,525 B2 | 8/2010 | Yano | |
| 8,318,823 B2 | 11/2012 | Triouleyre | |
| 8,735,460 B2 | 5/2014 | Knoblock et al. | |
| 2002/0090453 A1 | 7/2002 | Muthiah | |
| 2003/0093050 A1 * | 5/2003 | Baker | A61F 13/15203 604/378 |
| 2006/0030632 A1 | 2/2006 | Krueger | |
| 2006/0148907 A1 | 7/2006 | Nicholson | |
| 2007/0014947 A1 | 1/2007 | Mengel | |
| 2007/0179210 A1 | 8/2007 | Swaniker | |
| 2009/0281268 A1 * | 11/2009 | Rukavina | B32B 17/1077 528/60 |
| 2010/0228209 A1 | 9/2010 | Carlucci | |
| 2011/0110996 A1 | 5/2011 | Schoenberger | |
| 2012/0053547 A1 | 3/2012 | Schroeder | |
| 2012/0078154 A1 | 3/2012 | Pigg | |
| 2012/0175556 A1 | 7/2012 | Rudolf | |
| 2013/0171393 A1 | 7/2013 | Kannankeril | |
| 2013/0274349 A1 | 10/2013 | Qin | |

FOREIGN PATENT DOCUMENTS

| | | |
|---|---|---|
| EP | 2409673 | 1/2012 |
| JP | 2858660 | 2/1999 |
| JP | 3060095 | 7/2000 |
| JP | 2007-530820 | 3/2005 |
| JP | 2011-139897 | 7/2011 |
| WO | WO 9615748 | 5/1996 |
| WO | WO 1996-23024 | 8/1996 |
| WO | WO 9640633 | 12/1996 |
| WO | WO 9959719 | 11/1999 |
| WO | WO 20132227 | 5/2001 |
| WO | WO 2009123910 | 10/2009 |
| WO | WO 2013-180832 | 12/2013 |
| WO | WO 2013-180937 | 12/2013 |
| WO | WO 2013-188083 | 12/2013 |

OTHER PUBLICATIONS

Adhesives, Coatings and Elastomers, Isocyanate Product Line 2010, Huntsman, 2010, 2 pages.
ARCOL® E-434, Polyether Polyol, Bayer Material Science Product Information, 1 page.
CARPOL® GP-700 Polyether Polyol, Technical Data Sheet, CAS No. 25791-96-2, Carpenter Co., Chemicals Division, Jun. 2011, 2 pages.
Dabco® BA100 Blocking Agent, Polyurethane Additives Product Bulletin, 2011, 2 pages.
DOW Specialty Amines, TEA Fast Facts, Ethanolamine—TEA, Dow Chemical Company, 2012, 1 page.
LiquiBlock™ HS Fines, Technical Data, Emerging Technologies Inc., 1 page.
Ludewig, "Allophanate Structures as Building Blocks for Very Low Viscous Urethane Acrylates", RadTech Europe 2005 Conference & Exhibition, 2005, 6 pages.
Lundquist, "MCS-533 : 5/32" Polycril 400 Foam on Liner", CS-05-000533, 3M, Apr. 7, 2009, 12 pages.
Polyether Polyol, Technical Data Sheet, CDB-33142, Chemicals Division, Carpenter Co., Jan. 2012, 2 pages.
Rigid Foam High Density Molded, Dabco® Product List, Air Products, 2012, 1 page; commercially available prior to May 29, 2012.
Rubinate® 1245 MDI, Modified Polymeric Diphenylmethane Diisocyanate, Technical Data Sheet, Huntsman, 2010, 3 pages.
Rubinate®/Suprasec® MDI Specialty Isocyanates, Huntsman, 2 pages.

(56) References Cited

OTHER PUBLICATIONS

Silicones, Dabco® Product List, Air Products, 2012, 2 pages; commercially available prior to May 29, 2012.
Skok, "New Modified Liquid Pure MDI for CASE Applications", Huntsman Polyurethanes, 9 pages.
International Search Report for PCT International Application No. PCT/US2013/035390 dated Jun. 21, 2013, 4 pages.
The Polyurethanes Book, edited by David Randall and Stephen Lee (2002), chapters 6, 13, and 14, 52 pages.

* cited by examiner

ABSORBENT ARTICLE COMPRISING POLYMERIC FOAM AND INTERMEDIATES

CROSS REFERENCE TO RELATED APPLICATIONS

This application is a national stage filing under 35 U.S.C. 371 of PCT/US2013/035390, filed Apr. 5, 2013, which claims priority to U.S. Provisional Application No. 61/787,888, filed Mar. 15, 2013 and U.S. Provisional Application No. 61/652,388, filed May 29, 2012, the disclosure of which is incorporated by reference in their entirety herein.

BACKGROUND OF THE INVENTION

In the field of disposable absorbent articles, "superabsorbent polymers" (SAP) mixed with cellulose fibers provides a good means for storing aqueous fluids. However, such material has also been described as not enhancing fluid transport. When a phenomena often referred to as "gel-blocking" takes place, a reduction in fluid transport can occur.

Thus, many absorbent core designs have been described comprising components or layers with separate functionality, i.e. a liquid storage material and also a different material that provides acquisition and distribution of the fluid ("ADL").

Open celled polymeric foams have been described for use in disposable absorbent articles. One type of foam that has been described is made from high internal phase emulsions (also referred to as "HIPE"). Polyurethane foams have also been described for use in disposable absorbent articles.

SUMMARY

Although various absorbent articles have been described, industry would find advantage in alternative absorbent articles, particularly those having improved properties.

In one embodiment, an absorbent article is described comprising an absorbent composite disposed between a fluid pervious topsheet and a fluid impervious backsheet. The absorbent composite comprises a first absorbent layer comprising a polymeric foam having an average cell size of at least 100 microns. The polymeric foam has at least one property selected from a) an indentation force deflection of less than 75 N at 50%; or b) a constant deflection compression set of less than 25% for a deflection of 50%; or a combination of a) and b); and a second absorbent layer in fluid communication with the fluid transport layer.

In another embodiment, a polyurethane foam is described having an average cell size of at least 100 microns. The polyurethane foam comprises the reaction product of at least one polyol component having polyethylene oxide units and a polyisocyanate component that comprises at least 75 wt-% of at least one polymeric polyisocyanate that lacks urethane linkages. In some embodiments, the polyurethane foam is free of superabsorbent polymer. In some embodiments, the polyurethane foam has an average cell size up to 500 microns. In some embodiments, the polyurethane foam comprises at least 12 wt-% ethylene oxide units.

In another embodiment, an absorbent article is described comprising an absorbent composite. The absorbent composite comprises a first absorbent layer comprising a polymeric foam, the polymeric foam free of superabsorbent polymer and having an average cell size of at least 100 microns. The absorbent composite further comprises a second absorbent layer having an average absorption capacity of at least 20 g/g in fluid communication with the fluid transport layer.

Also described are various composites comprising the polyurethane foam described herein in combination with another substrate such as a second absorbent layer, a fluid impervious backsheet, and/or a fluid pervious topsheet.

DETAILED DESCRIPTION

Figure 1:
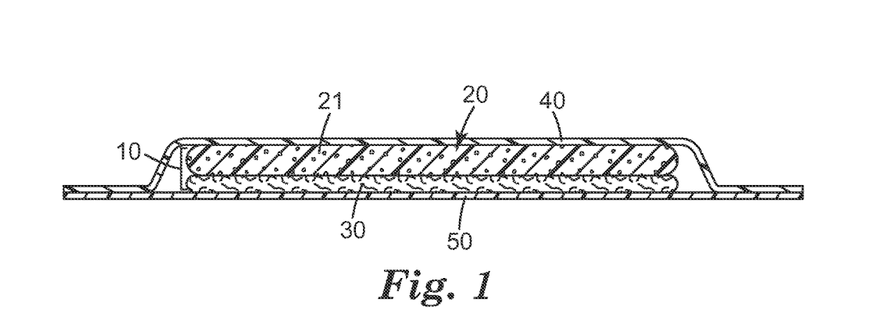
FIGS. 1-4 are cross-sectional views of absorbent articles comprising an absorbent composite, the absorbent composite having various arrangements of first and second absorbent layers.

With reference to FIG. 1, a cross-sectional view of an absorbent article comprising an absorbent composite 10 disposed between a fluid pervious topsheet 40 and fluid impervious backsheet 50. The absorbent composite comprises a first absorbent layer 20 and a second absorbent layer 30 in fluid communication with each other. The first absorbent layer comprises a polymeric foam 21. The layers are sufficiently proximate (i.e. near to) each other such that fluid from the first layer is readily transported to the second layer. In some embodiments, the first and second layers are in direct contact with each other. In other embodiments, one or more additional layers are disposed between the first and second layer. Such additional layer or layers do not detract from the intended properties of the absorbent composite (e.g. such as absorption capacity, strike-through, and rewet). In one embodiment, a tissue layer is disposed between the first and second absorbent layers. Favored absorbent articles include feminine hygiene articles, disposable diapers, and adult incontinence articles.

In a favored embodiment, the first absorbent layer functions as and thus will be referred to as a "fluid transport layer". Fluid transport layers quickly absorb the liquid through the absorbent article's top sheet for temporary retention (e.g., to act as a temporary reservoir), and to transfer that liquid into the underlying second absorbent layer at a rate at which the second absorbent layer can absorb for final or permanent retention. The fluid transport typically improves "wicking" of the absorbent article by spreading the body fluid in the "x" and "y" plane over the area of the second absorbent layer covered by the fluid transport layer while also carrying the fluid in the "z" direction to the second absorbent layer.

The absorbent composite comprises a first absorbent layer comprising a polymeric foam material. The polymeric foam comprises a continuous phase of a hydrophilic polymer. By "continuous" it is meant that the cell structure is substantially continuous, lacking discernible boundaries within the cell structure. In contrast, a layer formed from foam particles would be characterized as comprising a discontinuous layer since a plurality of discrete boundaries would be evident between neighboring foam particles. The foam of the absorbent composite optionally comprises discrete pieces of superabsorbent polymer dispersed within the polymeric foam. When present, the discrete pieces of superabsorbent polymer are typically homogeneously distributed within the polymeric foam.

The polymeric foams described herein are predominantly open-celled. This means the individual cells of the foam are in complete, unobstructed communication with adjoining cells. The cells in such substantially open-celled foam structures have intercellular openings or "windows" that are large enough to permit fluid transfer from one cell to the other within the foam structure. The individual cells may be defined by a plurality of mutually connected, three dimensionally branched webs. The strands of polymeric material making up these branched webs can be referred to as "struts." A foam material is typically "open-celled" if at least 80% of the cells in the foam structure that are at least 1 micrometer in size are in fluid communication with at least one adjacent cell. Thus, a portion of the cells (up to 20%) of the foam may be closed. The minimum cell size is typically at least 5, 10, 15, 20, 25, or 30 micrometers.

In addition to being open-celled, the polymeric foams are sufficiently hydrophilic to permit the foam to absorb aqueous fluids. The internal surfaces of the foam structures can be rendered hydrophilic by the selection of (e.g. hydrophilic) components during the formation of the polymeric foam or by post-treatment.

The average cell size of the total foam structure is typically at least 100 microns. In some embodiments, the average cell size is at least 110, 120, 130, 140, or 150 microns. The average cell is typically no greater than 1000, 900, 800, or 700 microns. In some embodiments, the average cell size may be no greater than 650 microns, 600 microns, 550 microns, 500 microns, 450 microns, 400 microns, 350 microns, or 300 microns. As used herein, average cell size refers to the average cell size as determined using a scanning electron microscope at a magnification of 50×, as further described in the examples.

In some embodiments, the foam has a relatively uniform cell size. For example, the average cell size on one major surface may be about the same or vary by no greater than 10% as compared to the opposing major surface. In other embodiments, the average cell size of one major surface of the foam may differ from the opposing surface. For example, in the foaming of a thermosetting material it is not uncommon for a portion of the cells at the bottom of the cell structure to collapse resulting in a lower average cell size on one surface. When the foam has a gradient of average cell size, it is preferred that the surface having the smaller average cell size is in fluid communication with the second (e.g. fluid storage) absorbent layer.

The foam is typically a non-collapsed foam. A non-collapsed foam typically does not substantially expand upon contact with aqueous fluids, such as body fluids.

In favored embodiments, the foam of the (e.g. fluid transport) first absorbent layer is a polyurethane foam. Polyurethane polymers are generally formed by the reaction of at least one polyisocyanate component and at least one polyol component. The polyisocyanate component may comprise one or more polyisocyanates. The polyol component may comprise one or more polyols. The concentration of a polyol may be expressed with regard to the total polyol component. The concentration of polyol or polyisocyanate may alternatively be expressed with regard to the total polyurethane concentration.

Various aliphatic and aromatic polyisocyanates have been described in the art. The polyisocyanate utilized for forming the polyurethane foam typically has a functionality between from 2 and 3. In some embodiments, the functionality is no greater than about 2.5.

In one embodiment, the foam is prepared from at least one aromatic polyisocyanate. Examples of aromatic polyisocyanates include those having a single aromatic ring such as are toluene 2,4 and 2,6-diisocyanate (TDI) and naphthylene 1,5-diisocyanate; as well as those having at least two aromatic rings such as diphenylmethane 4,4'-, 2,4'- and 2,2'- diisocyanate (MDI).

In favored embodiments, the foam is prepared from one or more (e.g. aromatic) polymeric polyisocyanates. Polymeric polyisocyanates typically have a (weight average) molecular weight greater than a monomeric polyisocyanate (lacking repeating units), yet lower than a polyurethane prepolymer. Thus, the polyurethane foam is derived from at least one polymeric polyisocyanate that lacks urethane linkages. In other words, the polyurethane foam is derived from a polymeric isocyanate that is not a polyurethane prepolymer. Polymeric polyisocyanates comprises other linking groups between repeat units, such as isocyanurate groups, biuret groups, carbodiimide groups, uretonimine groups, uretdione groups, etc. as known in the art.

Some polymeric polyisocyanates may be referred to as "modified monomeric isocyanate". For example pure 4,4'-methylene diphenyl diisocyanate (MDI) is a solid having a melting point of 38° C. and an equivalent weight of 125 g/equivalent. However, modified MDIs, are liquid at 38° C. and have a higher equivalent weight (e.g. 143 g/equivalent). The difference in melting point and equivalent weight is believed to be a result of a small degree of polymerization, such as by the inclusion of linking groups, as described above.

Polymeric polyisocyanates, including modified monomeric isocyanate, may comprise a mixture of monomer in combination with polymeric species inclusive of oligomeric species. For example, polymeric MDI is reported to contain 25-80% monomeric 4,4'-methylene diphenyl diisocyanate as well as oligomers containing 3-6 rings and other minor isomers, such as 2,2' isomer.

Polymeric polyisocyanates typically have a low viscosity as compared to prepolymers. The polymeric isocyanates utilized herein typically have a viscosity no greater than about 300 cps at 25° C. and in some embodiments no greater than 200 cps or 100 cps at 25° C. The viscosity is typically at least about 10, 15, 20 or 25 cps at 25° C.

The equivalent weight of polymeric polyisocyanates is also typically lower than that of prepolymers. The polymeric isocyanates utilized herein typically have an equivalent weight of no greater than about 250 g/equivalent and in some embodiments no greater than 200 g/equivalent or 175 g/equivalent. In some embodiments, the equivalent weight is at least 130 g/equivalent.

The average molecular weight (Mw) of polymeric polyisocyanates is also typically lower than that of polyurethane prepolymers. The polymeric isocyanates utilized herein typically have an average molecular weight (Mw) of no greater than about 500 Da and in some embodiments no greater than 450, 400, or 350 Da.

In some embodiments, the polyurethane is derived from a single polymeric isocyanate or a blend of polymeric isocyanates. Thus, 100% of the isocyanate component is polymeric isocyanate(s). In other embodiments, a major portion of the isocyanate component is a single polymeric isocyanate or a blend of polymeric isocyanates. In these embodiments, at least 50, 60, 70, 75, 80, 85 or 90 wt-% of the isocyanate component is polymeric isocyanate(s).

Some illustrative polyisocyanates include for example, polymeric MDI diisocyanate from Huntsman Chemical Company, The Woodlands, Tex., under the trade designation "RUBINATE 1245"; and modified MDI isocyanate available from Huntsman Chemical Company under the trade designation "SUPRASEC 9561".

The aforementioned isocyanates are reacted with a polyol to prepare the polyurethane foam material. The polyurethane foams are hydrophilic, such that the foam absorbs aqueous liquids, particularly body fluids. The hydrophilicity of the polyurethane foams is typically provided by use of an isocyanate-reactive component, such as a polyether polyol, having a high ethylene oxide content. Examples of useful polyols include adducts [e.g., polyethylene oxide, polypropylene oxide, and poly(ethylene oxide-propylene oxide) copolymer] of dihydric or trihydric alcohols (e.g., ethylene glycol, propylene glycol, glycerol, hexanetriol, and triethanolamine) and alkylene oxides (e.g., ethylene oxide, propylene oxide, and butylene oxide). Polyols having a high ethylene oxide content can also be made by other techniques as known in the art. Suitable polyols typically have a molecular weight (Mw) of 100 to 5,000 Da and contain an average functionality of 2 to 3.

The polyurethane foam is typically derived from (or in other words is the reaction product of) at least one polyether polyol having ethylene oxide (e.g. repeat) units. The polyether polyol typically has an ethylene oxide content of at least 10, 15, 20 or 25 wt-% and typically no greater than 75 wt-%. Such polyether polyol has a higher functionality than the polyisocyanate. In some embodiments, the average functionality is about 3. The polyether polyol typically has a viscosity of no greater than 1000 cps at 25° C. and in some embodiments no greater than 900, 800, or 700 cps. The molecular weight of the polyether polyol is typically at least 500 or 1000 Da and in some embodiments no greater than 4000 or 3500, or 3000 Da. Such polyether polyol typically has a hydroxyl number of at least 125, 130, or 140. An illustrative polyol includes for example a polyether polyol product obtained from the Carpenter Company, Richmond, Va. under the designations "CDB-33142 POLYETHER POLYOL", "CARPOL GP-5171", and EB-PO-11034-1"

In some embodiments, one or more polyether polyols having a high ethylene oxide content and a molecular weight (Mw) of no greater than 5500, or 5000, or 4500, or 4000, or 3500, or 3000 Da, as just described, are the primary or sole polyether polyols of the polyurethane foam. For example, such polyether polyols constitute at least 50, 60, 70, 80, 90, 95 or 100 wt-% of the total polyol component. Thus, the polyurethane foam may comprise at least 25, 30, 35, 40, 45 or 50 wt-% of polymerized units derived from such polyether polyols.

In other embodiments, one or more polyether polyols having a high ethylene oxide content are utilized in combination with other polyols. In some embodiments, the other polyols constitute at least 1, 2, 3, 4, or 5 wt-% of the total polyol component. The concentration of such other polyols typically does not exceed 40, or 35, or 30, or 25, or 20, or 15, or 10 wt-% of the total polyol component, i.e. does not exceed 20 wt-%, or 17.5 wt-%, or 15 wt-%, or 12.5 wt-%, or 10 wt-%, or 7.5 wt-%, or 5 wt-% of the polyurethane. Illustrative other polyols include a polyether polyol product (Chemical Abstracts Number 25791-96-2) that can be obtained from the Carpenter Company, Richmond, Va. under the designation "CARPOL GP-700 POLYETHER POLYOL" and a polyether polyol product (Chemical Abstracts Number 9082-00-2) that can be obtained from Bayer Material Science, Pittsburgh, Va. under the trade designation "ARCOL E-434". In some embodiments, such optional other polyols may comprise polypropylene (e.g. repeat) units.

The polyurethane foam generally has an ethylene oxide content of at least 10, 11, or 12 wt-% and no greater than 20, 19, or 18 wt-%. In some embodiments, the polyurethane foam has an ethylene oxide content of no greater than 17 or 16 wt-%.

The kinds and amounts of polyisocyanate and polyol components are selected such that the polyurethane foam is relatively soft, yet resilient. These properties can be characterized for example by indentation force deflection and constant deflection compression set, as measured according to the test methods described in the examples. In some embodiments, the polyurethane foam has an indentation force deflection of less than 75N at 50%. The indentation force deflection at 50% may be less than 70N, or 65N, or 60 N. In some embodiments, the polyurethane foam has an indentation force deflection of less than 100N at 65%. The indentation force deflection at 65% may be less than 90N, or 80N, or 70 N, or 65N, or 60N. In some embodiments, the indentation force deflection at 50% or 65% is typically at least 30N or 35N. The constant deflection compression set at 50% deflection can be zero and is typically at least 0.5, 1 or 2% and generally no greater than 35%. In some embodiments, the constant deflection compression set at 50% deflection is no greater than 30%, or 25%, or 20%, or 15%, or 10%.

The polyurethane foam may comprise known and customary polyurethane formation catalysts such as organic tin compounds and/or an amine-type catalyst. The catalysts are preferably used in an amount of from 0.01 to 5 wt-% of the polyurethane. The amine-type catalyst is typically a tertiary amine. Examples of suitable tertiary amine include monoamines such as triethylamine, and dimethyl cyclohexylamine; diamines such as tetramethylethylenediamine, and tetramethylhexanediamine; triamines such as tetramethylguanidine; cyclic amines such as triethylenediamine, dimethylpiperadine, and methylmorphorine; alcoholamines such as dimethylaminoethanol, trimethylaminoethylethanolamine, and hydroxyethylmorphorine; ether amines such as bisdimethylaminoethyl ethanol; diazabicycloalkenes such as 1,5-diazabicyclo(5,4,0)undecene-7 (DBU), and 1,5-diazabicyclo(4,3,0)nonene-5; and organic acid salts of the diazabicycloalkenes such as phenol salt, 2-ethylhexanoate and formate of DBU. These amines can be used either singly or in combination. The amine-type catalyst can be used in an amount no greater than 4, 3, 2, 1 or 0.5 wt-% of the polyurethane.

The polyurethane typically comprises a surfactant to stabilize the foam. Various surfactants have been described in the art. In one embodiment a silicone surfactant is employed that comprises ethylene oxide (e.g. repeat) units, optionally in combination with propylene oxide (e.g. repeat) units such as commercially available from Air Products under the trade designation "DABCO DC-198". In some embodiments, the concentration of hydrophilic surfactant typically ranges from about 0.05 to 1 or 2 wt-% of the polyurethane.

The polyurethane foam may comprise various additives such as surface active substances, foam stabilizers, cell regulators, blocking agents to delay catalytic reactions, fire retardants, chain extenders, crosslinking agents, external and internal mold release agents, fillers, pigments (titanium dioxide), colorants, optical brighteners, antioxidants, stabilizers, hydrolysis inhibitors, as well as anti-fungal and anti-bacteria substances. Such other additives are typically collectively utilized at concentrations ranging from 0.05 to 10 wt-% of the polyurethane.

In some embodiments, the absorbent foam is white in color. Certain hindered amine stabilizers can contribute to discoloration, such as yellowing, of the absorbent foam. In some embodiments, the absorbent foam is free of diphenylamine stabilizer and/or phenothiazine stabilizer.

In other embodiments, the absorbent foam may be a colored (i.e. a color other than white). The white or colored absorbent foam can include a pigment in at least one of the components. In preferred embodiments, pigment is combined with a polyol carrier and is added to the polyol liquid stream during manufacture of the polyurethane foam. Commercially available pigments include for example DispersiTech™ 2226 White, DispersiTech™ 2401 Violet, DispersiTech™ 2425 Blue, DispersiTech™ 2660 Yellow, and DispersiTech™ 28000 Red from Milliken in Spartansburg, S.C. and Pdi® 34-68020 Orange from Ferro in Cleveland, Ohio.

In the production of polyurethane foams, the polyisocyanate component and polyol component are reacted such that an equivalence ratio of isocyanate groups to the sum of hydroxyl groups is no greater than 1 to 1. In some embodiments, the components are reacted such that there are excess hydroxyl groups (e.g. excess polyol). In such embodiments, the equivalence ratio of isocyanate groups to the sum of the hydroxy groups is at least 0.7 to 1. For example, the ratio may be at least 0.75:1, or at least 0.8:1.

Polyurethane foams can be prepared by mixing the reactants in liquid form with a suitable amount of water or chemical blowing agent, suitable catalyst and other optional components, and allowing the mixture to foam and set. It is preferred to use water for producing the polyurethane foams, because the water reacts with the isocyanate groups to liberate carbon dioxide. The amount of water is preferably in the range from 0.5 to 5% wt-% polyurethane. In some embodiments, the amount of water is no greater than 4 or 3 or 2 or 1 wt-% polyurethane.

Polyurethane foam can be made by various methods as described in the art. In one embodiment, the polyurethane foams are generally prepared by continuous casting of a thin layer of foam onto a substrate, such as described in U.S. Pat. No. 2,957,207. Although U.S. Pat. No. 2,957,207 emphasizes the importance of introducing a limited delay after the polyol component and polyisocyanate component have been mixed, such delay is not typically utilized when the foam is conveyed between a pair of metering rolls such that the gap setting of the metering rolls controls the thickness of the foam. The foam is typically cured at an over temperature ranging from about 100° F. to 275° F. Alternatively the foam can be made as blocks that are cut to the desired thickness or by casting the foam in an open or closed metallic mold.

The (e.g. polyurethane) polymeric foam of the first absorbent (e.g. fluid transport) layer may optionally comprise a superabsorbent polymer (SAP), also referred to as "hydrogels" and "hydrocolloids", such as described in patent application Ser. No. 61/652,408, filed May 29, 2012. The SAP is substantially water-insoluble, but water-swellable polymers capable of absorbing large quantities of liquids (e.g. 10-100 times their weight). Various SAP materials have been described in the art. (See for example U.S. Pat. Nos. 4,410,571; 6,271,277; and 6,570,057; incorporated herein by reference.) These include superabsorbents with low gel strength, high gel strength, surface cross-linked superabsorbents, uniformly cross-linked superabsorbents, or superabsorbents with varied cross-link density throughout the structure. Superabsorbents may be based on chemistries that include poly(acrylic acid), poly(iso-butylene-co-maleic anhydride), poly(ethylene oxide), carboxy-methyl cellulose, poly(-vinyl pyrrolidone), and poly(-vinyl alcohol). The superabsorbents may range in swelling rate from slow to fast. The superabsorbents may be in various degrees of neutralization. Counter-ions are typically Li, Na, K, Ca. Favored SAP materials can be slightly network cross-linked polymers of partially neutralized polyacrylic acids or starch derivatives thereof. For example, the SAP may comprise from about 50 to about 95%, preferably about 75%, neutralized, slightly network crosslinked, polyacrylic acid (i.e. poly (sodium acrylate/acrylic acid)). As described in the art, network crosslinking serves to render the polymer substantially water-insoluble and, in part, determines the absorptive capacity and extractable polymer content characteristics of the precursor particles and the resultant macrostructures.

For embodiments wherein the foam comprises SAP, the SAP is generally present within the foam as discrete pieces. Such pieces may have various shapes such as spherical, rounded, angular, or irregular pieces as well as fibers. The particles generally comprise a distribution of sizes ranging from about 1 micron to 500 microns in diameter or cross-section (largest dimension when not spherical). The particles are preferably a finely divided powder of a maximum particle size of less than 400, 300, or 200 microns.

When present, the concentration of SAP in the polymeric foam is typically at least 1, 2, 3, 4, or 5 wt-% of the (e.g. polyurethane) polymeric composition and typically no greater than 30, 25, or 20 wt-% of the (e.g. polyurethane) polymeric composition. The minimal amount of SAP that can provide the desired properties (e.g. absorption capability, strike-through, rewet) is utilized. In some embodiments, the concentration of SAP is no greater than 17.5, or 15, or 12.5 or 10 wt-% of the (e.g. polyurethane) polymeric composition. In some embodiments, the inclusion of the SAP in the foam has little or no affect on the absorption capacity of the foam, yet surprisingly improves the strikes through and rewet of the foam and especially the absorbent composite.

The SAP particles can be incorporated into the polymeric foam by mixing the SAP with the ingredients used for making foam. In the direct addition of the SAP during the production of the (e.g. polyurethane) polymeric foams, the SAP is typically added to the polyol component. However, other methods for incorporating the SAP into the polymeric foams have also been described, such as described in U.S. Pat. No. 6,271,277.

For embodiments wherein the foam comprises SAP, the SAP is typically homogeneously distributed within the polymeric material of the first absorbent layer. However, the first absorbent layer may comprise more than one layer, wherein the layers have a different concentration of SAP. For example, a polymeric foam layer having a lower concentration of SAP may be proximate the topsheet and a polymeric foam layer having a higher concentration may be proximate the second absorbent layer.

The hydrophilic (e.g. polyol(s)) component(s) of the (e.g. polyurethane) polymeric foam provide the desired absorption capacity of the foam. Thus the foam may be free of superabsorbent polymer. Further, the polyurethane foam is free of amine or imine complexing agent such as ethylenimine, polyethylenimine, polyvinylamine, carboxy-methylated polyethylenimines, phosphono-methylated polyethylenimines, quaternized polyethylenimines and/or dithiocarbamitized polyethylenimines; as described for example in U.S. Pat. Nos. 6,852,905 and 6,855,739.

The polymeric (e.g. polyurethane) foam typically has an average basis weight of at least 100, 150, 200, or 250 gsm and typically no greater than 500 gsm. In some embodiments the average basis weight is no greater than 450, or 400 gsm. The average density of the (e.g. polyurethane) polymeric foam is typically at least 3, 3.5 or 4 lbs/ft$^3$ and no greater than 7 lbs/ft$^3$.

The (i.e. uncompressed) thickness of the foam-containing first absorbent (e.g. fluid transport) layer is at least 0.1 millimeters and typically no greater than about 10 millimeters. In some embodiments, the thickness is between about 1 millimeters and about 5 millimeters. A skilled artisan will appreciate that the preferred thickness may vary depending on the particular size of absorbent garment, and its intended use. For example, for larger babies and adults, a higher absorption capacity material typically is needed.

The first and second absorbent layers and absorbent composite can have various shapes including symmetrical (having a point, line, or plane of symmetry) or unsymmetrical shapes. Shapes that are envisioned include but are not limited to circles, ovals, squares, rectangles, pentagons, hexagons, octagons, trapezoids, truncated pyramids, hourglasses, dumbbells, dog bones, etc. The edges and corners can be straight or rounded. The sides can be curved (convex or concave), tapered, flared, or angled. In some embodiments, the absorbent composite has an hour-glass or trapezoid shape.

The second absorbent layer can have the same size and shape as the first absorbent layer. In this embodiment, substantially an entire major surface of the first absorbent layer (e.g. polymeric foam) is in contact with or in fluid communication with the second absorbent layer. Alternatively, the second absorbent layer can have a different size and/or shape than the first absorbent layer. In some embodiments, the second absorbent layer has a length and/or width that is less than the length and/or width of the first absorbent layer (e.g. polymeric foam). Thus, a portion of the first absorbent layer (e.g. polymeric foam) is not in contact with or in fluid communication with the second absorbent layer. Typically the second absorbent layer is arranged such that it is in contact with or in fluid communication with the central region of the first absorbent layer (e.g. polymeric foam). Thus, when the second absorbent layer has a length and/or width that is less than the first absorbent layer (e.g. polymeric foam), opposing perimeter regions or the entire perimeter region of the first absorbent layer (e.g. polymeric foam) is not in contact with or in fluid communication with the second absorbent layer. In some embodiments, the surface area of the major surface of the second absorbent layer that faces and is fluid communication with the first absorbent layer (e.g. polymeric foam) ranges from about one/half to three/fourths (e.g. about two/thirds) of the total surface area of the major surface of the first absorbent layer (e.g. polymeric foam) facing the second absorbent layer. In one embodiment, the first absorbent layer (e.g. polymeric foam) has an hour-glass shape and the second absorbent layer is a rectangular strip spanning the central longitudinal axis of the hour-glass, the rectangular strip having a width slightly less than the narrowest (middle) portion of the hour-glass.

The foam can contain cut-out regions that create voids, cavities, depressions, channels, or grooves. In one embodiment, at least the central region of the foam comprises a plurality of circular perforations having a diameter of about 1 mm, spaced about 3 mm apart.

The first and/or second absorbent layers and/or the absorbent composite may comprise various functional additives including for example, antimicrobial coatings, ion capturing coatings, desiccants, fragrance, and odor control particles.

Regardless of the shape, the first and second absorbent layers and absorbent composite can generally be defined as having a first major face, an opposing second major face substantially parallel to the first major face, and a thickness in a direction orthogonal to the first and opposing major face.

In some favored embodiments, the first absorbent layer functions as a fluid transport layer and the second absorbent layer functions as the fluid storage layer. Other layers, such as a tissue layer, may be disposed between the first absorbent (e.g. fluid transport) layer and second absorbent (e.g. fluid storage) layer. The presence of these other layers do not detract from and typically have little effect on the properties of the absorbent composite. In such embodiments, the second absorbent layer has at least the same and typically a higher absorption capacity than the first absorbent layer. For example, the second absorbent layer typically has an average absorption capacity of at least 20, 21, 22, 23, 24 g/g or at least about 25-30 g/g (i.e. at least 25, 26, 27, 28, 29, or 30 g/g) or at least 8 g/cc. In some embodiments, the second absorbent layer has an average absorption capacity of no greater than 60 or 55 or 50 or 45 or 40 g/g. The first absorbent layer has an average absorption capacity of at least 10 g/g; yet typically less than 20 or 15 g/g. Further the first absorbent layer has an average absorption capacity of at least 1 g/cc, but typically less than or equal to 2 g/cc.

The second absorbent material can be made of a variety of materials. In some embodiments, the second absorbent material is the same or similar (e.g. polyurethane) polymeric foam having more SAP than the first absorbent layer. In another embodiment, the second absorbent layer comprises fibrous materials, typically in the form of a fibrous web.

Although the fluid transport layer and fluid storage layer are both absorbent, the fluid storage layer has a considerably greater absorption capacity than the fluid transport layer. In one embodiment, the absorption capacity (g/g or g/cc) of the second layer is at least 1.5×, 2×, 2.5×, or even 3× the absorption capacity of the first absorbent layer (i.e. X). In some embodiments, the absorption capacity of the second layer is typically no greater than 5× or 4.5× or 4×.

The fibers of the second (e.g. fluid storage) layer are hydrophilic, or can be a combination of both hydrophilic and hydrophobic fibers. Suitable fibers include those that are naturally occurring fibers (modified or unmodified), as well as synthetically made fibers. Examples of suitable unmodified/modified naturally occurring fibers include cotton, Esparto grass, bagasse, hemp, flax, silk, wool, wood pulp, chemically modified wood pulp, jute, rayon, ethyl cellulose, and cellulose acetate.

Suitable wood pulp fibers can be obtained from known chemical processes such as, but not limited to the Kraft and sulfite processes. A further suitable type of fibers is chemically stiffened cellulose, i.e., stiffened by chemical means to increase the stiffness of the fibers under both dry and aqueous conditions. Such means can include the addition of a chemical stiffening agent that, for example, coats and/or impregnates the fibers or by stiffening of the fibers by altering the chemical structure, e.g., by crosslinking polymer chains, as known in the art. Curl may be imparted to the fibers by methods including chemical treatment or mechanical twisting. Curl is typically imparted before crosslinking or stiffening.

Hydrophilic fibers, particularly (optionally modified) cellulosic fibers are typically preferred. However, hydrophilic fibers can also be obtained by hydrophilizing hydrophobic fibers, such as surfactant-treated or silica-treated thermoplastic fibers. Surfactant-treated fibers can be made by spraying the fiber with a surfactant, by dipping the fiber into a surfactant or by including the surfactant as part of the polymer melt in producing the thermoplastic fiber. Upon melting and resolidification, the surfactant will tend to remain at the surfaces of the thermoplastic fiber.

Suitable synthetic fibers can be made from polyvinyl chloride, polyvinyl fluoride, polytetrafluoroethylene, polyvinylidene chloride, polyacrylics, polyvinyl acetate, polyethylvinyl acetate, non-soluble or soluble polyvinyl alcohol, polyolefins such as polyethylene and polypropylene, polyamides such as nylon, polyesters, polyurethanes, polystyrenes, and the like. In some embodiments, the synthetic fibers are thermoplastic, e.g. having a melt point of at least 50° C.-75° C. less and no greater than 190 or 175° C.

Generally the (e.g. thermoplastic) synthetic fibers have an average width, diameter, or cross-section dimension of at least 5, 10, 15, or 20 microns. The average diameter may range up to 1000 microns (1 mm), yet is typically no greater than 800 microns, or 700 microns, or 600 microns, and in some embodiments no greater than 500 microns or 400 microns. In some embodiments, the average diameter of the fibers of the web is no greater than 300, 250, 200, 150, 100, 75 or 50 microns. Smaller diameter staple fiber webs can provide improved flexibility (e.g. a lower work of compression). The filament cross sectional dimension (and shape of the cross section) is preferably substantially, or essentially, uniform along the length of the filament, e.g., uniformly round. The surface of the filament is typically smooth. The fibers can be in the shape or form of fibers, strips, or other narrow and long shapes. Aggregations can be made up of a plurality of fibers with the same or different plastic compositions, geometric shapes, sizes, and/or diameters. The fibers are typically solid. The fibers can be circular or round in cross section or non-circular in cross section, e.g., lobal, elliptical, rectangular, triangular, and shapes with radial arms such as "x-shaped". For embodiments wherein a thermoplastic fiber is formed from melt-extrusion processes (e.g. spunbond or melt blown) the length of the fibers is continuous. The length of the staple fibers (i.e. fibers) is typically at least 1, 2, or 3 cm, and commonly no greater than 15 cm. In some embodiments, the length of the fibers is no greater than 10, 9, 8, or 7 cm.

The fluid storage layer may be a preformed fibrous web. There are a variety of "dry-laid' and "wet-laid" web-making processes described in the art. Various second (e.g. fluid storage) layers and methods of making such have been described in the art. (See for example U.S. Pat. Nos. 4,610,678 and 6,896,669)

In some embodiments, the second (e.g. fluid storage) layer is typically a highly absorbent material that comprises superabsorbent polymer. In some embodiment, the second layer comprises discrete pieces of superabsorbent polymer, such as the previously described discrete pieces of SAP, optionally included in the polymeric foam. The second absorbent layer may be substantially free of superabsorbent fiber or rayon/superabsorbent fiber. The second (e.g. fluid storage) layer may comprise a blend of cellulosic fibers and superabsorbent material. One illustrative second (e.g. fluid storage) layer has a basis weight from about 100 g/m$^2$ to about 700 g/m$^2$ which has been air-laid as a bottom layer of pulp, a middle layer of pulp and superabsorbent polymer disposed in amongst the pulp, and a top layer containing at least some pulp. The second absorbent layer or material may have a density of 0.25 or 0.3 g/cc to about 0.5 g/cc.

The second (e.g. fluid storage) layer typically comprises at least 5 or 10 wt-% and preferably at least 15, 20, 25 or 30 wt-% of superabsorbent polymer. The superabsorbent polymer is typically no greater than 75 wt-% of the second (e.g. fluid storage) layer and in some embodiments, no greater than 55, 50, 45, or 40 wt-%. The second (e.g. fluid storage) layer may have a basis weight of at least 150 to 200 g/m$^2$ and typically no greater than 500 g/m$^2$.

The second absorbent layer can have a basis weight less than, equal to, or greater than the (e.g. polyurethane) foam. The average basis weight of the composite may be at least 150, 200, 250, or 300 gsm and typically no greater than 1000 gsm. In some embodiments the average basis weight of the composite is no greater than 900, or 800 gsm, or 600 gsm.

The first absorbent (e.g. fluid transport) layer and second (e.g. fluid storage) layer can be joined together by any suitable technique. In one embodiment, the layers are joined together with an adhesive. Examples of suitable adhesives include emulsion, hot melt, curable, or solvent-based adhesives. Suitable pressure sensitive adhesives include (meth) acrylate-based pressure sensitive adhesives, such as those described in U.S. Pat. No. Re 24,906 (Ulrich), polyurethane adhesives, natural or synthetic rubber-based adhesives, epoxy adhesives, curable adhesives, phenolic adhesives, and the like.

There are various ways in which the first absorbent layer can be utilized (e.g. as a fluid transport element) proximate a second absorbent layer, some of which are depicted in FIGS. 1-4. FIGS. 1-4, depict cross-sectional views of an absorbent article comprising absorbent composite 10 disposed between a fluid pervious topsheet 40 and fluid impervious backsheet 50. The absorbent composite comprises various arrangements of a first absorbent layer 20 and a second absorbent layer 30 in fluid communication with each other. The first absorbent layer comprises a polymeric foam 21.

In some embodiments, such as depicted in FIG. 1 the first absorbent layer 20 comprises a continuous layer of the polymeric foam and the second absorbent layer 30 comprises a continuous layer of a fluid storage material, such as cellulosic fiber and SAP. In this embodiment, the first absorbent layer has about the same cross-sectional width as the second absorbent layer.

Figure 2:
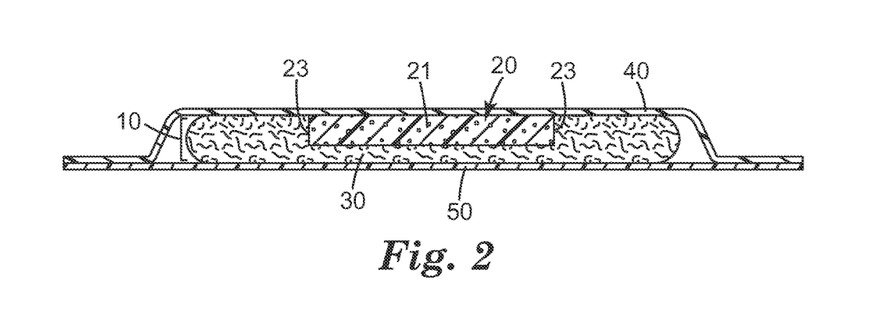

In other embodiments, the cross-sectional width of the first absorbent layer is less than the width of the second absorbent layer. For example, FIG. 2 depicts the polymeric foam 21 inserted within the second absorbent layer 30 such that substantially all the lateral edges 23 (i.e. faces orthogonal to the major surfaces that define the thickness of the polymeric foam) of foam 21 are in fluid communication with the second absorbent layer 30.

Figure 3:
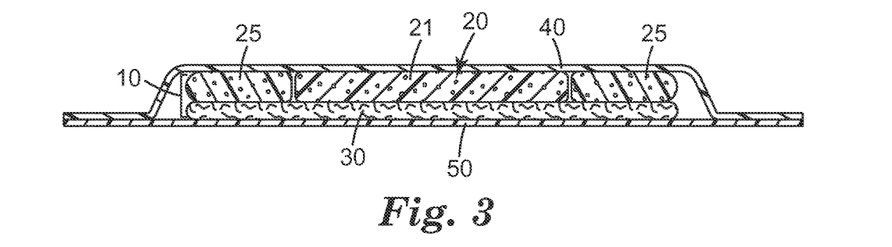

FIG. 3 depicts a multi-component first absorbent layer comprising polymeric foam 21 in a central region 20 and a different fluid transport material 25 disposed on opposing sides of the central region. In one embodiment, fluid transport material 25 may comprise a foam having a different (e.g. higher) SAP content than 20. Alternatively, fluid transport material 25 may comprise a commercially available material used for acquisition layers in disposable absorbent articles such as air bond staple fibers, adhesively bonded staple fibers, and thermally point bonded staple fibers. In yet another embodiment, the central region 20 may comprise a different fluid transport material with the fluid transport material of the opposing sides 25 comprising the polymeric foam as described herein.

Figure 4:
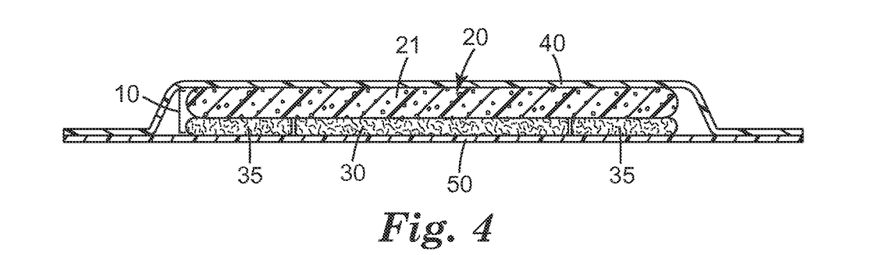

FIG. 4 depicts a multi-component second absorbent layer wherein a SAP containing cellulosic fiber web 30 is present in a central region and a different fluid storage material 35 disposed on opposing sides of the central region. In one embodiment, fluid storage material 35 may comprise an absorbent foam.

In yet other embodiments, (not shown) both the first absorbent layer 20 and the second absorbent layer may both comprise multi-components.

The absorbent composite typically has an absorption capacity of at least 10, 11, 12, 13, 14, 15, 16, 17, 18, 19 or 20 g/g. The absorbent composite typically has an absorption capacity of at least 1, 1.1, 1.2, 1.3, 1.4, 1.5, 1.6, 1.7, 1.8, 1.9, 2.0, 2.1, or 2.2 g/cc. The absorption capacity of the absorbent composite is typically no greater than the second layer. The absorbent composite can exhibit a strike through of less than 20, 15, or 10, 9, 8, 7, 6 and in some embodiments 5 seconds. In favored embodiments, the strike through is no greater than 4.5, or 4, or 3.5, or 3.0, or 2.5, or 2.0 seconds. In some favored embodiments, the strike through is less than 2.0 seconds. The composite can exhibit a rewet less than 2 or 1.5. or 1.0 grams. In some embodiments, the rewet is less than 0.9, 0.8, 0.7, and in some embodiments 0.6 or 0.5 or 0.4, or 0.3 grams. The composite can exhibit various combinations of the absorption capacity, strike though, and rewet properties just described. The various numerical values expressed for absorption capacity, strike though, and rewet described herein refer to the average absorption capacity, average strike though, and average rewet unless specified otherwise.

The composite typically has an absorption capacity greater than the polymeric foam. Further, the composite typically has an absorption capacity less than the second absorbent layer. The strike through of the composite is lower (better than) the second absorbent layer. In some embodiments, the strike though is lower than the polymeric foam. Thus, the composite can have a strike though lower than either individual layer. The rewet of the composite is significantly lower (better than) the polymeric foam. In some embodiments, the rewet of the composite is lower than the second absorbent layer. The composite can exhibit good absorption capacity in combination with improved strike through and/or improved rewet.

The absorbent composite of the first (e.g. foam) absorbent layer and the second (e.g. fibrous) absorbent layer can be utilized as an absorbent article, such as suitable for use for spill containment or medical uses, such as wound dressings. In other embodiments, such as a disposable diaper, a feminine hygiene article, or adult incontinence article, the absorbent composite may further comprise another substrate, such as a fluid pervious topsheet and/or a fluid impervious backsheet.

The topsheet 40 is typically the body-facing surface of the absorbent article. Thus, the topsheet comes in contact with a wearer's skin during use of the absorbent article. The topsheet is typically compliant, soft feeling, and non-irritating to the wearer's skin. Further, the topsheet is liquid pervious, permitting liquids to readily penetrate through its thickness. Suitable topsheets may be manufactured from a wide range of materials, such as porous foams, reticulated foams, apertured plastic films, natural fibers (e.g., wood or cotton fibers), synthetic fibers (e.g., polyester or polypropylene fibers) or from a combination of natural and synthetic fibers. The topsheet is typically a hydrophobic material to isolate the wearer's skin from liquids in the absorbent material. Thus, the topsheet is typically a different material than the underlying first absorbent foam layer.

There are a number of manufacturing techniques which may be used to manufacture the topsheet. The topsheet may be woven, non-woven, spunbonded, carded, or the like. An illustrative topsheet is carded, and thermally bonded (1.5 denier polypropylene staple fibers). The topsheet may have a basis weight from about 18 to about 25 grams per square meter. Further, the topsheet typically has a minimum dry tensile strength of at least about 400 grams per centimeter in the machine direction and a wet tensile strength of at least about 55 grams per centimeter in the cross machine direction.

The backsheet 50 is impervious to liquids and typically is a thin plastic film, although other liquid impervious materials may also be used. The backsheet is typically flexible, meaning that it is compliant and will readily conform to the general shape and contours of the wearer's body. The backsheet prevents the exudates absorbed and contained in the absorbent material from wetting articles which contact the absorbent article such as bed sheets and undergarments. One illustrative backsheet is polyethylene film having a thickness of from about 0.012 mm (0.5 mil) to about 0.051 centimeters (2.0 mils). The backsheet may be embossed and or matte finished to provide a more clothlike appearance. Further, the backsheet may permit vapors to escape from the absorbent member while still preventing exudates from passing through the backsheet.

In a typical disposable absorbent article, the topsheet and backsheet are associated together in any suitable manner. Typically, the topsheet and the backsheet are affixed directly to each other at the periphery of the article by an attachment means such as an adhesive or any other attachment means as known in the art.

The disposable absorbent article may comprise a variety of other features as known in the art. For example, when the disposable absorbent article is a feminine hygiene or an adult incontinence napkin (also referred to as a "pad"), the article may further comprise wings or flaps as described for example in U.S. Pat. No. 5,472,437 (3M, Akiyama); U.S. Pat. No. 5,730,739 (P&G, Lavash); and U.S. Pat. No. 5,201,727 (Kao Corp., Nakanishi). Feminine hygiene or adult incontinence napkins also typically comprise a pressure sensitive adhesive on the outer surface of the liquid impervious backsheet for bonding the napkin to an undergarment. Further, when the disposable absorbent article is a disposable diaper, the article may further comprise elasticized leg openings. Disposable diapers also typically comprise a means of attaching the front and rear regions such as by use of adhesive tape or mechanically interlocking hook and loop fasteners.

Test Methods

Sample Thickness:

Sample thickness was measured in millimeters by placing a metric ruler or caliper along the z-axis of sample and recording the thickness. When a caliper was used, care was taken to insure that the sample was not compressed. For more precise measurements, the sample was placed onto a stage and a Keyence model VHX-600E digital stereo microscope (Keyence Corporation, Itasca, Ill.) was rotated 90 degrees in line and centered with the z-plane of the sample. A metric ruler was adhered to the stage and adjacent to the z-plane of the foam as a reference. A scale was calibrated using the reference and the sample thickness was measured using ImageJ software (a public domain imaging program). Sample measurements were made in triplicate with the mean value reported.

Cell Size (Microns):

The average diameter of the cells in a polyurethane foam standard was determined using a FEI XL30 Environmental Scanning Electron Microscope (ESEM), operating in high vacuum mode (available from the FEI Company, Hillsboro, Oreg.). The foam standard was cross-sectioned (in the direction perpendicular to the first major surface of the foam sheet) by cutting with a scalpel while the sample was sitting on dry ice and the cross-sectioned face was imaged at a magnification of 50×. The images were analyzed using ImageJ software. A total of 60-75 cell diameters were measured at random points across the cross-sectioned sample with the mean value being reported. For each cell, the longest dimension was measured. However, holes in cell walls were not measured. The average cell diameter for the polyurethane foam standard was 233 microns.

By comparing the other exemplified foams to the foam standard using a microscope (30× magnification), it was determined that these other foams had an average cell diameters of about the same size as the foam standard.

Basis Weight (Gsm):

A rule die measuring 5.08 cm×5.08 cm (2 inch×2 inch) was used to cut the sample for basis weight measurement. The sample was weighed and the basis weight subsequently calculated. Sample measurements were made in triplicate with the mean value reported.

Absorption Capacity:

Saline solution (90 mL of 0.9% NaCl in deionized water) was poured into a 100 ml disposable Petri dish. A 5.08 cm×5.08 cm (2 inch×2 inch) sample was weighed and recorded as "dry weight". The sample was immersed into the Petri dish and allowed to saturate for 5 minutes. The sample was removed by using tweezers to hold a corner of the sample. The sample was suspended vertically to drip dry for 2 minutes. The wet weight was recorded and the absorption capacity was calculated using the following equations:

Absorption Capacity (g/g)=[(wet sample weight−dry sample weight)/dry sample weight]

The absorption capacity per unit volume of dry sample was calculated using the following formula:

Absorption Capacity (g/cc)=[(wet sample weight−dry sample weight)/dry sample volume]

All sample measurements were made in triplicate and reported as the mean value.

Strike Through Time (Sec):

The strike through time was measured using the saline solution and a test jig. The jig was made of plexiglass with the dimensions of 10.16 cm×10.16 cm×2.54 cm (4 inch×4 inch×1 inch). A 2.54 cm hole (1 inch) was cut in the center of the plexiglass jig. The test jig weighed about 284 grams. Unless specified otherwise, the test sample was at least 10.16 cm×10.16 cm. The test sample was placed under the test jig and positioned so that the hole in the plexiglass was directly above the center of the sample. Saline solution (10 mL of 0.9% NaCl in deionized water) was poured into the hole and the time (in seconds) required for the saline solution to penetrate into the test sample was recorded. To enhance visualization, the saline solution was dyed with red food coloring. The test samples were oriented so that the polyurethane foam layer was in direct contact with the plexiglass surface of the test jig. In this orientation, the polyurethane foam layer was the first surface of the test sample to come in contact with the saline solution. Sample measurements were made in triplicate and reported as the mean value.

Rewet (g):

The rewet measurement was determined using the same test jig as described for the strike through time measurement. Unless specified otherwise, the test sample was at least 10.16 cm×10.16 cm. The test sample was placed under the test jig and positioned so that the hole in the plexiglass was directly above the center of the sample. The test samples were oriented so that the polyurethane foam layer was in direct contact with the plexiglass surface of the test jig. In this orientation, the polyurethane foam layer was the first surface of the test sample to come in contact with the saline solution. Saline solution (10 mL of 0.9% NaCl in deionized water) was poured into the hole and the sample was maintained in the test jig for 5 minutes. The test jig was removed and a stack of ten sheets of WHATMAN #4 90 mm filter paper was placed on top of the test sample. Prior to placement on the sample, the stack of filter paper was weighed to obtain an initial weight. The test jig was reapplied to the sample and a 2200 gram weight was placed and centered on top of the plexiglass test jig (providing a loading of 3827 Pa (0.56 psi) for 15 seconds. The assembly was removed and the stack of filter paper was weighed again to obtain a final weight. The rewet measurement was calculated using the following equation: Rewet (g)=final filter paper weight−initial filter paper weight. All sample measurements were made in triplicate and reported as the mean value.

Indentation Force Deflection (N):

The indentation force deflection test (IFD) was conducted in accordance with ASTM D3574-08 with the following modifications. The dimension of the sample was 160 mm by 160 mm and the dimensions of the platens were 150 mm by 150 mm. A contact force of 2.5 N was used.

The IFD was measured at deflections of 25%, 50%, and 65%. All sample measurements were made in triplicate and reported as the mean value. A digital caliper was used to measure the foam thickness.

Constant Deflection Compression Set (%):

The constant deflection compression set test was conducted in accordance with ASTM D3574-08 for 50% deflection of the initial thickness. The sample dimension was 50.8 mm by 50.8 mm and multiple foam sheets were stacked to achieve an overall sample thickness of about 25 mm. The metal plates of the test apparatus were 250 mm by 250 mm by 10 mm and secured with the inclusion of a spacer element so that the bottom surface of the upper plate was positioned 12.5 mm from the top surface of the lower plate. The sample was secured in the tightened apparatus and maintained in an oven at 37.8° C. (100° F.) for 22 hours.

The compression set ($C_t$) measurements were made in triplicate and reported as the mean value. A digital caliper was used to measure the foam thickness.

Materials

Polymeric diphenylmethane diisocyanate (polymeric MDI) was obtained from Huntsman Chemical Company, The Woodlands, Tex., under the trade designation "RUBINATE 1245". The "RUBINATE 1245" material was reported to have the following properties: average Mw of 283 Da, equivalent weight of 128 g/equivalent, functionality of 2.21, % isocyanate content of 32.8, specific gravity at 25° C. of 1.23, and viscosity at 25° C. of 25 cps.

Modified diphenylmethane diisocyanate (MDI) was obtained from Huntsman Chemical Company, The Woodlands, Tex., under the trade designation "SUPRASEC 9561". The "SUPRASEC 9561" material was reported to have the following properties: equivalent weight of 143 g/equivalent, functionality of 2.10, % isocyanate content of 29.3, specific gravity at 25° C. of 1.21, and a viscosity at 25° C. of 36 cps.

The first polyether polyol product was obtained from the Carpenter Company, Richmond, Va. under the designation "CDB-33142". The polymer was a blend prepared from glycerine, propylene oxide, and ethylene oxide. The "CDB-33142" was reported to have the following properties: average Mw of 2300 Da, average Mn of 1200 Da, hydroxyl number of 142, functionality of 3, ethylene oxide content of 26%, and a viscosity at 25° C. of 500 cps.

The second polyether polyol product was obtained from the Carpenter Company, Richmond, Va. under the trade designation "CARPOL GP-700". The polymer was prepared from glycerine, propylene oxide. The "CARPOL GP-700" was reported to have the following properties: average Mw of 730-770 Da, average Mn of 700 Da, hydroxyl number of 240, functionality of 3, ethylene oxide content of 0, and a viscosity at 25° C. of 250 cps.

The third polyether polyol product was obtained from the Bayer MaterialScience, Pittsburgh, Va. under the trade designation "ARCOL E-434". The polymer was prepared as a polyoxy-propylene triol modified with ethylene oxide. The "ARCOL E-434" was reported to have the following properties: average Mw of 4800 Da, hydroxyl number of 33.8-37.2, ethylene oxide content of 15%, and a viscosity at 25° C. of 820 cps.

The fourth polyether polyol product was obtained from the Carpenter Company, Richmond, Va. under the trade designation "CARPOL GP-5171". The polymer was a glycerine initiated polyether polyol polymerized with propylene oxide and ethylene oxide and then capped with 15% ethylene oxide. The "CARPOL GP-5171" was reported to have the following properties: average Mw of 5100 to 5500 Da, hydroxyl number of 35, functionality of 3, ethylene oxide content of 71%, and a viscosity at 25° C. of 1.2 cps.

The fifth polyether polyol product was obtained from the Carpenter Company, Richmond, Va. under the designation "EB-PO-11034-1". EB-PO-11034-1 was reported to have the following properties: average Mw of 3000 Da, average Mn of 1300 Da, hydroxyl number of 133, and an ethylene oxide content of 49%.

Triethanolamine LFG (low freeze grade), 85% triethanolamine and 15% water was obtained from Quaker Chemica, Conshohocken, Pa., under the trade designation "TEA99LFG". The solution of triethylene diamine (33 weight percent) in dipropylene glycol was obtained from the Air Products Company, Allentown, Pa., under the trade designation "DABCO 33-LV". The tertiary amine catalyst used to catalyze the urea formation reaction (water with isocyanate) was obtained from the Air Products Company under the trade designation "DABCO BL-17".

The trade designated compounds "DABCO DC-198, a silicone glycol copolymer surfactant, and "DABCO BA-100", a polymeric acid blocking agent used for delaying the catalytic reaction, were obtained from the Air Products Company.

Gelok 5040-72, an absorbent tissue core component composed of a layer of superabsorbent polymer (about 60% by weight) placed between two layers of cellulosic fiber tissue (about 40% by weight), was obtained from Gelok International, Dunbridge, Ohio. The Gelok 5040-72 had a thickness of 0.3 mm and an average basis weight of 86 gsm.

Control (Second Absorbent Layer (Gelok 5040-72) without Foam)

The Gelok 5040-72 absorbent core was evaluated excluding all other components. The core was on average 0.3 mm thick and had an average basis weight of 90 gsm. The absorption capacity was 27.97 g/g (8.37 g/cc); the strike through time was 36.9 seconds; and the rewet was 0.11 grams.

Example 1

The open cell polyurethane foam layer was prepared by adding the MDI SUPRASEC 9561 (58.2 parts) to a mixture of CDB-33142 (100 parts), CARPOL GP-700 (3.0 parts), water (1.0 parts), triethanolamine LFG (3.7 parts), DABCO DC-198 (2.0 parts), ARCOL E-434 (4.0 parts), DABCO 33-LV (0.45 parts), DABCO BA-100 (0.12 parts), and DABCO BL-17 (0.10 parts). All the components were at room temperature 70° F. (21° C.) with the exception that CDB-33142 was at 40° F. (4.4° C.). The polyol components were premixed for about 15 seconds and then mixed with the MDI for an additional 10-12 seconds. The mixture was immediately poured onto polypropylene coated release paper (14 mils thick). A second sheet of polypropylene coated release paper contacted the opposing surface of the foam as it was conveyed between a pair of metering rolls. After thin sheet casting and oven curing at 100° C. for 5 minutes, the resulting sheet of polyurethane open cell foam was measured to be on average 3.5 mm thick, with an average density of 0.090 g/cc (5.64 lbs/ft$^3$). The average basis weight of the foam was 316 gsm. The results from the Indentation Force Deflection and the Constant Deflection Compression Set Tests for Example 1 are reported in Tables A and B.

Control Example 1

A thin sheet casted open cell polyurethane foam layer was prepared as described in Example 1 by adding the MDI SUPRASEC 9561 (72.7 parts) to a mixture of CDB-33142 (100 parts), CARPOL GP-700 (3.0 parts), water (1.0 parts), triethanolamine LFG (3.7 parts), DABCO DC-198 (2.0 parts), ARCOL E-434 (4.0 parts), DABCO 33-LV (0.45 parts), DABCO BA-100 (0.12 parts), and DABCO BL-17 (0.10 parts). The resulting sheet of polyurethane open cell foam was measured to be on average 3.1 mm thick, with an average density of 0.071 g/cc (4.43 lbs/ft$^3$). The average basis weight of the foam was 249 gsm. The results from the Indentation Force Deflection and the Constant Deflection Compression Set Tests for Control Example are reported in Tables A and B.

TABLE A

Indentation Force Deflection Test

| Example Number | Sample Thickness (mm) | Force at 25% Deflection (N) | Force at 50% Deflection (N) | Force at 65% Deflection (N) |
|---|---|---|---|---|
| Example 1 | 3.6 | 48.6 | 50.5 | 54.4 |
| Control Example 1 | 3.1 | 52.0 | 108.3 | 160.1 |

TABLE B

Constant Deflection Compression Set Test at 50% Deflection

| Example Number | Original Sample Thickness (mm) | Sample Thickness at End of Test (mm) | Compression Set (Ct) (%) |
|---|---|---|---|
| Example 1 | 25.0 | 24.0 | 4 |
| Control Example 1 | 25.0 | 13.5 | 46 |

Absorbent Composite Example 1

The open cell polyurethane foam layer of Example 1 was adhesively laminated to Gelok 5040-72 using Spray 77 adhesive, available from the 3M Company, St. Paul, Minn. The bi-layer construction was on average 3.8 mm thick, and had an average basis weight of 413 gsm. The absorption capacity was 14.50 g/g (1.71 g/cc); the strike through time was 5.4 seconds; and the rewet was 0.78 grams.

Control Absorbent Composite 1

The open cell polyurethane foam layer of Control Example 1 was adhesively laminated to Gelok 5040-72 using Spray 77 adhesive. The bi-layer construction was on average 3.4 mm thick, and had an average basis weight of 371 gsm. The absorption capacity was 15.10 g/g (1.81 g/cc); the strike through time was 13.0 seconds; and the rewet was 0.27 grams.

TABLE C

| Example Number | Absorption Capacity (g/g) | Absorption Capacity (g/cc) | Strike Through (seconds) | Rewet (grams) |
| --- | --- | --- | --- | --- |
| Absorbent Composite Example 1 | 14.50 | 1.71 | 5.4 | 0.78 |
| Control Absorbent Composite 1 | 15.10 | 1.81 | 13.0 | 0.27 |

Absorbent Composite Example 2

A thin sheet casted open cell polyurethane foam layer was prepared as described in Example 1 by adding the polymeric MDI RUBINATE 1245 (54.5 parts) to a mixture of CDB-33142 (100 parts), CARPOL GP-700 (2.4 parts), water (1.2 parts), triethanolamine LFG (3.7 parts), DABCO DC-198 (2.0 parts), ARCOL E-434 (4.0 parts), DABCO 33-LV (0.45 parts), DABCO BA-100 (0.12 parts), and DABCO BL-17 (0.10 parts). The resulting polyurethane open cell cast foam was measured to be on average 3.0 mm thick, with an average density of 0.094 g/cc (5.85 lbs/ft$^3$). The average basis weight of the foam was 280 gsm.

A sample of polyurethane foam (alone without Second Absorbent Layer) was measured to have an absorption capacity of 11.00 g/g (1.03 g/cc); strike through time of 6.3 seconds; and rewet of 7.99 grams.

The foam layer was adhesively laminated to Gelok 5040-72 using Spray 77 adhesive. The bi-layer construction was on average 3.3 mm thick, and had an average basis weight of 388 gsm. The absorption capacity was 13.03 g/g (1.54 g/cc); the strike through time was 4.6 seconds; and the rewet was 0.60 grams.

Comparative Absorbent Composite Example 1
(Foam with Average Cell Diameter of 22 Microns)

The two layer High Internal Phase Emulsion (HIPEs) foam absorbent core of a commercially available ALWAYS INFINITY HEAVY FLOW feminine hygiene pad (Proctor & Gamble Co., Cincinnati, Ohio) was removed from the topsheet and backsheet of the pad and evaluated independent of any adjacent layer component. The HIPEs foam layers each had a different cell diameter. The upper HIPEs foam layer of the absorbent core component had an average cell diameter of 22 microns. The lower HIPES foam layer of the absorbent core component had an average cell diameter of 6 microns. The HIPEs foam core was measured to be on average 2.5 mm thick, with an average density of 0.080 g/cc (5.01 lbs/ft$^3$). The average basis weight was 201 gsm. The absorption capacity was 20.26 g/g (1.63 g/cc).

The HIPEs foam from the pad contained cut-outs to facilitate fluid strike through performance. To determine the performance of the foam independent of cut-outs, the cut-outs were covered with a minimum amount of masking tape (using only enough tape to block the openings). A 7.62 cm×15.24 cm (3 inch×6 inch) sample was prepared for strike through and rewet testing by splicing with masking tape two 7.62 cm×7.62 cm (3 inch×3 inch) absorbent core sections cut from the rear half of two pads. For strikethrough time and rewet measurements, the HIPEs foam core was oriented in the test jig so that upper HIPEs foam layer was in direct contact with the plexiglass surface of the test jig. The strike through time was 24.3 seconds, and the rewet was 2.19 grams.

Control Absorbent Composite Example 2

Foam of Comparative Example 1 with Second Absorbent Layer of Absorbent Composite Examples 1 & 2

The two layer HIPEs foam absorbent cores were removed from ALWAYS INFINITY HEAVY FLOW feminine hygiene pads. A 7.62 cm×15.24 cm sample was prepared by splicing with masking tape two 7.62 cm by 7.62 cm absorbent core sections cut from the rear half of two pads (as described in Comparative Example 1).

The constructed HIPEs foam sample was adhesively laminated to Gelok 5040-72 using Spray 77 adhesive. The orientation of the two layer HIPEs foam as found in the commercial article was preserved by laminating the backsheet facing surface of the HIPEs foam to the Gelok 5040-72. The product of the finished construction was on average 2.8 mm thick and had an average basis weight of 322 gsm. The absorption capacity was 18.73 g/g (2.15 g/cc).

For strike through time and rewet measurements, the cut-outs in the HIPEs foam were covered with a minimum amount of masking tape (as described in Comparative Example 1). The product of the finished construction was oriented so that the HIPEs foam was in direct contact with the plexiglass surface of the test jig. In this orientation, the HIPEs foam was the first surface of the test sample to come in contact with the saline solution. The strike through time was 21.4 seconds; and the rewet was 1.43 grams.

Comparative Wound Dressing

Samples of Tegaderm™ High Performance Foam Adhesive Dressing, Product No. 90612 were obtained. A cross section of such product consists of an absorbent foam layer having a thickness of 3.2 mm, a second absorbent layer having a thickness of 2 mm consisting of rayon/superabsorbent fibers, and an adhesive-coated conformable barrier film. The adhesive coated conformable barrier film was left intact for testing the absorption capacity and removed for testing strike through and rewet.

The absorbent foam is a polyurethane foam containing 3.16-3.21 wt-% of superabsorbent particles. The absorbent foam had an average basis weight of 350 gsm and a cell diameter of 1057 microns+/−341. The second absorbent layer had an absorption capacity of 18.6 g/g and 2.2 g/cc. The bi-layer composite construction had an average basis weight of 619 gsm.

TABLE D

Absorbent Composites with Second Absorbent Layer A

| Example Number | Absorption Capacity (g/g) | Absorption Capacity (g/cc) | Strike Through (seconds) | Rewet (grams) |
| --- | --- | --- | --- | --- |
| Absorbent Composite Example 1 | 14.50 | 1.71 | 5.4 | 0.78 |
| Absorbent Composite Example 2 | 13.02 | 1.54 | 4.6 | 0.60 |

TABLE D-continued

Absorbent Composites with Second Absorbent Layer A

| Example Number | Absorption Capacity (g/g) | Absorption Capacity (g/cc) | Strike Through (seconds) | Rewet (grams) |
|---|---|---|---|---|
| Comparative Absorbent Composite Example 1 | 20.26 | 1.63 | 24.3 | 2.19 |
| Control Absorbent Composite Example 2 | 18.73 | 2.15 | 21.4 | 1.43 |
| Comparative Wound Dressing | 9.49 | 1.23 | 9.7 | 0.94 |

By comparing Absorbent Composite Examples 1-2 to Comparative Example 1 (a commercially available product), it is evident that Absorbent Composite Examples 1-2 have reduced strike through and rewet. By comparing Absorbent Composite Examples 1-2 to Control Example 2 (utilizing the same second absorbent layer), it is evident that the polyurethane foam layer provides the reduced strike through and rewet.

Other polyurethane foams that can be thin sheet casted as described in Example 1 having about the same cell size as the standard foam and believed to have similar Indentation Force Deflection and the Constant Deflection Compression Set at 50% Deflection properties as Example 1 are described as follows:

Example 3

The open cell polyurethane foam layer can be prepared by adding the MDI SUPRASEC 9561 (60.7 parts) to a mixture of the polyether polyol CDB-33142 (100 parts), CARPOL GP-5171 (5.4 parts), Arcol E-434 (4.0 parts), water (1.2 parts), triethanolamine LFG (3.7 parts), DABCO DC-198 (0.2 parts), DABCO 33-LV (0.45 parts), DABCO BA-100 (0.12 parts), and DABCO BL-17 (0.10 parts).

Example 4

The open cell polyurethane foam layer can be prepared by adding the MDI SUPRASEC 9561 (61.0 parts) to a mixture of CDB-33142 (100 parts), CARPOL GP-700 (3.6 parts), ARCOL E-434 (4.0 parts), water (1.2 parts), triethanolamine LFG (3.7 parts), DABCO DC-198 (2.0 parts), DABCO 33-LV (0.45 parts), DABCO BA-100 (0.12 parts), and DABCO BL-17 (0.10 parts).

Example 5

The open cell polyurethane foam layer can be prepared by adding the MDI SUPRASEC 9561 (60.5 parts) to a mixture of CDB-33142 (75 parts), EB-PO-11034-1 (25 parts), CARPOL GP-700 (3.6 parts), Arcol E-434 (4.00 parts), water (1.2 parts), triethanolamine LFG (3.7 parts), DABCO DC-198 (2.0 parts), DABCO 33-LV (0.45 parts), DABCO BA-100 (0.12 parts), and DABCO BL-17 (0.10 parts).

What is claimed is:

1. An absorbent article comprising:
   an absorbent composite disposed between a fluid pervious topsheet and a fluid impervious backsheet wherein the absorbent composite comprises:
   a first absorbent layer comprising a polyurethane foam having an average cell size of at least 100 microns wherein the polymeric foam has
   a) an indentation force deflection of less than 75 N at 50% for an area of 150 mm by 150 mm; and
   b) a constant deflection compression set of less than 25% for a deflection of 50%; and
   a second absorbent layer in fluid communication with the first absorbent layer.

2. The absorbent article of claim 1 wherein the article is a disposable diaper, a feminine hygiene article, or adult incontinence article.

3. The absorbent article of claim 1 wherein the average cell size of the polyurethane foam is no greater than 500 microns.

4. The absorbent article of claim 1 wherein the polyurethane foam is free of superabsorbent polymer.

5. The absorbent article of claim 1 wherein the first absorbent layer is a fluid transport layer and the second absorbent layer has a higher absorption capacity than the first absorbent layer.

6. The absorbent article of claim 1 wherein the second absorbent layer is selected from a fibrous layer, a foam layer, or a combination thereof.

7. The absorbent article of claim 6 wherein the fibrous layer comprises cellulosic fiber.

8. The absorbent article of claim 7 wherein the second absorbent layer comprises a superabsorbent polymer.

9. The absorbent article of claim 1 wherein the article further comprises a tissue layer between the first and second absorbent layers.

10. The absorbent article of claim 1 wherein the composite has an absorption capacity of at least 10 g/g.

11. The absorbent article of claim 1 wherein the composite has an absorption capacity of at least 1 g/cc.

12. The absorbent article of claim 1 wherein the composite has a strike through of no greater than 15 seconds.

13. The absorbent article of claim 1 wherein the composite has a rewet of no greater than 1 gram.

14. The absorbent article of claim 1 wherein the polyurethane foam is derived from a silicone surfactant having ethylene oxide units.

15. The absorbent article of claim 1 wherein the polyurethane foam is free of amine or imine complexing agent.

16. The absorbent article of claim 1 wherein the polyurethane foam comprises the reaction product of at least one polyol having polyethylene oxide units and a polyisocyanate component, wherein at least 75 wt-% of the polyisocyanate component comprises polymeric polyisocyanate that lacks urethane linkages.

17. The absorbent article of claim 1 wherein the polyurethane foam comprises at least 12 wt-% ethylene oxide units.

18. The absorbent article of claim 1 wherein the second absorbent layer has an average absorption capacity of at least 20 g/g.

19. The absorbent article of claim 1 wherein the second absorbent layer has an average absorption capacity of at least 30 g/g.

* * * * *

UNITED STATES PATENT AND TRADEMARK OFFICE
CERTIFICATE OF CORRECTION

PATENT NO. : 10,357,588 B2
APPLICATION NO. : 14/394109
DATED : July 23, 2019
INVENTOR(S) : Delton Thompson, Jr. et al.

Page 1 of 1

It is certified that error appears in the above-identified patent and that said Letters Patent is hereby corrected as shown below:

On the Title Page

Item (57), Column 2,
Line 10, delete "the a" and insert -- a --, therefor.

In the Specification

Column 5,
Line 31, delete "EB-PO-11034-1'"" and insert -- "EB-PO-11034-1". --, therefor.

Column 6,
Lines 28 & 29, delete "dimethylpiperadine," and insert -- dimethylpiperidine, --, therefor.
Line 29, delete "methylmorphorine;" and insert -- methylmorpholine; --, therefor.
Line 31, delete "hydroxyethylmorphorine;" and insert -- hydroxyethylmorpholine; --, therefor.

Column 11,
Line 39, after "6,896,669)'"" insert -- . --.

Column 14,
Lines 8 & 9, delete "and or" and insert -- and/or --, therefor.

Column 17,
Line 28, delete "Chemica," and insert -- Chemical, --, therefor.

Signed and Sealed this
Seventeenth Day of September, 2019

Andrei Iancu
*Director of the United States Patent and Trademark Office*